United States Patent
Kim et al.

(10) Patent No.: US 8,193,355 B2
(45) Date of Patent: Jun. 5, 2012

(54) PROCESS FOR PREPARING SODIUM RISEDRONATE HEMIPENTAHYDRATE

(75) Inventors: Young-Deuck Kim, Suwon-si (KR); Jae-Yeon Shin, Yongin-si (KR)

(73) Assignee: Dongwoo Syntech Co., Ltd, Chungcheongbuk-Do (KR)

( * ) Notice: Subject to any disclaimer, the term of this patent is extended or adjusted under 35 U.S.C. 154(b) by 3 days.

(21) Appl. No.: 12/519,661

(22) PCT Filed: Oct. 22, 2007

(86) PCT No.: PCT/KR2007/005165
§ 371 (c)(1),
(2), (4) Date: Jun. 17, 2009

(87) PCT Pub. No.: WO2008/075831
PCT Pub. Date: Jun. 26, 2008

(65) Prior Publication Data
US 2010/0016592 A1   Jan. 21, 2010

(30) Foreign Application Priority Data
Dec. 20, 2006 (KR) .................. 10-2006-0130718

(51) Int. Cl.
*C07F 9/58* (2006.01)

(52) U.S. Cl. ........................................ 546/22

(58) Field of Classification Search .......... None
See application file for complete search history.

(56) References Cited

U.S. PATENT DOCUMENTS
2002/0002282 A1   1/2002   Cazer et al.
2003/0195170 A1   10/2003  Aronhime et al.

FOREIGN PATENT DOCUMENTS
| KR | 1020020071976 A | 9/2002 |
| KR | 1020040101447 A | 12/2004 |
| KR | 1020060054297 A | 5/2006 |
| WO | 2005012314 A1 | 2/2005 |
| WO | WO 2005082915 A1 * | 9/2005 |

OTHER PUBLICATIONS

Notes of K. Edwards, Ph.D., Univ. of Cal., "RDGcrystallization," May 2006.*

* cited by examiner

*Primary Examiner* — Janet Andres
*Assistant Examiner* — Timothy R Rozof
(74) *Attorney, Agent, or Firm* — Lucas & Mercanti, LLP

(57) ABSTRACT

A novel process for preparing risedronate sodium hemipentahydrate represented by the following formula 1 using 2-(3-pyridyl)-1-hydroxyethane-1,1-bisphosphonic acid (risedronic acid) and an aqueous solution of risedronate sodium is disclosed.

[Formula 1]

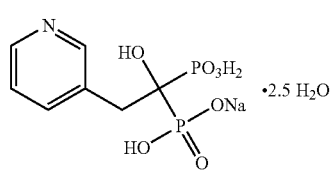

5 Claims, 2 Drawing Sheets

PROCESS FOR PREPARING SODIUM RISEDRONATE HEMIPENTAHYDRATE

This application is a 371 of PCT/KR/2007/005165 filed on Oct. 22, 2007, which claims the benefit of Korean Patent Application No. 10-2006-0130718 filed on Dec. 20, 2006, the contents of each of which are incorporated herein by reference.

TECHNICAL FIELD

The present invention relates to a novel process for preparing sodium risedronate hemipentahydrate represented by the following formula 1 using 2-(3-pyridyl)-1-hydroxyethane-1,1-bisphosphonic acid (risedronic acid) and an aqueous solution of risedronate sodium.

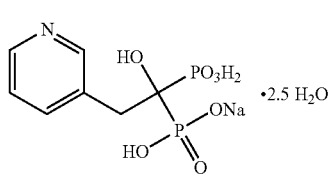

[Formula 1]

BACKGROUND ART

Osteoporosis is a disease that generates progressive loss of bone mineral. The object of therapy in treatment of osteoporosis is to improve calcium absorption and decrease urinary excretion of calcium. Bisphosphonates, such as 2-(3-pyridyl)-1-hydroxyethane-1,1-bisphosphonic acid (risedronic acid), are useful in the treatment of bone diseases and calcium metabolic diseases. Particularly, Paget's disease and heterotropic ossification are being treated by ethane-1-hydroxy-1,1-bisphosphonic acid (EHDP) and risedronate sodium represented by the following formula 2 at present.

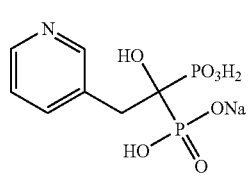

[Formula 2]

Korean Patent Application No. 10-2002-7009790 describes a selective crystallization of risedronate sodium as monohydrate (1 hydrate) or hemipentahydrate (2.5 hydrate). It discloses in that a crystalline form of monohydrate or hemipentahydrate may be selectively obtained from an aqueous solution of risedronate sodium according to the crystallization conditions, and that the crystalline form of hydrates is determined by the water and isopropanol ratio, the nucleating temperature controlled by varying the temperature, and the crystallization rate. Moreover, in the above-mentioned patent application, it discloses that the hemipentahydrate contains water in an amount of about 11.9% to about 13.9%, more preferably about 12.5% to about 13.2%, and most preferably 12.9% and is specified by various means, such as X-ray diffraction.

However, in order to selectively obtain hemipentahydrate according to the above-mentioned process, the nucleating temperature and the crystallization rate must be controlled, and particularly, a solvent in addition to purified water must be added. Thus, the process is complicated.

Further, Korean Patent Application No. 10-2006-7000683 includes the step of adjusting pH to supplement the above-mentioned patent application. However, it is disadvantageous in that the process is long and an inorganic acid must be used.

Korean Patent Application No. 10-2004-7016268 presents various hydrate forms such as A (hemipentahydrate), B, BB, B1, C, D, E, F, G, or H, a preparation method of each form, and results of X-ray diffraction, thermogravimetry analysis (TGA), and Fourier transform infrared spectroscopy (FTIR). However, the patent requires maintaining an aqueous solution of risedronate sodium at a reflux temperature, and is disadvantageous in that a solvent other than the aqueous solution of risedronate sodium must be added as in Korean Patent Application No. 10-2002-7009790.

DISCLOSURE

Technical Problem

Therefore, the present invention has been made in view of the above problems, the present invention is characterized by using 2-(3-pyridyl)-1-hydroxyethane-1,1-bisphosphonic acid (risedronic acid) as a reaction intermediate and solely purified water as a crystallization solvent.

As an inorganic base used to form risedronate sodium, NaOH, $NaHCO_3$, $Na_2CO_3$ may be used.

That is, the present invention relates to a novel process for selectively preparing risedronate sodium hemipentahydrate at an appropriate temperature by simply using a starting material (risedronic acid or risedronate sodium anhydride), purified water, and an inorganic base.

In the invention, "risedronic acid" is referred to as 2-(3-pyridyl)-1-hydroxyethane-1,1-bisphosphonic acid represented by the following formula 3.

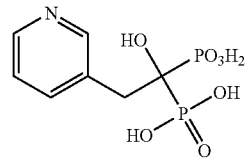

[Formula 3]

Moreover, risedronic acid is disclosed in U.S. Pat. No. 5,583,122 (Benedict et al.) published on Dec. 10, 1996 and assigned to the Procter & Gamble Co. and a Journal edited by IBC Technical Services ["An American Conference, Bisphosphonates: Current Status and Future Prospects" The Royal College of Physicians, London, England, May 21-22, 1990].

Technical Solution

In accordance with an aspect of the present invention, the above and other objects can be accomplished by the provision of a process for preparing risedronate sodium hemipentahydrate represented by formula 1, which comprises the steps of adding 2-(3-pyridyl)-1-hydroxyethane-1,1-bisphosphonic acid (risedronic acid) represented by formula 3 and an inorganic base to purified water and dissolving the mixture at a temperature of 50 to 80° C., cooling the solution to a temperature of 5 to 30° C. for crystallization, and filtering and vacuum drying to obtain a crystallized product.

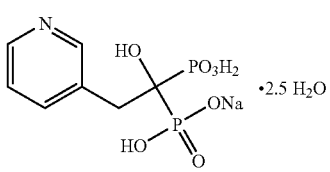

[Formula 1]

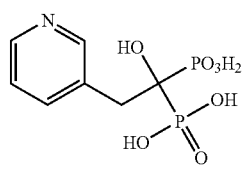

[Formula 3]

In accordance with another aspect of the present invention, there is provided a process for preparing risedronate sodium hemipentahydrate, which comprises the steps of dissolving risedronate sodium anhydride represented by formula 2 with purified water at a temperature of 60 to 80° C., and cooling the solution to a temperature of 5 to 25° C.

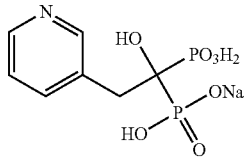

[Formula 2]

In accordance with yet another aspect of the present invention, there is provided a process for preparing risedronate sodium hemipentahydrate which comprises the step of exposing risedronate sodium anhydride at an atmospheric temperature of 30 to 40° C. and a relative humidity of 60 to 90% for 4 to 20 hours.

DESCRIPTION OF THE DRAWINGS

The above and other objects, features and other advantages of the present invention will be more clearly understood from the following detailed description taken in conjunction with the accompanying drawings, in which.

BEST MODE

The present invention relates to a process for preparing risedronate sodium hemipentahydrate using 2-(3-pyridyl)-1-hydroxyethane-1,1-bisphosphonic acid (risedronic acid) and an aqueous solution of risedronate sodium. The preparation process of risedronate sodium hemipentahydrate is very simple and carried out in a mild condition. Thus, the process is easily applied to industrial production.

The process for preparing risedronate sodium hemipentahydrate according to the present invention comprises the steps of:

adding 2-(3-pyridyl)-1-hydroxyethane-1,1-bisphosphonic acid (risedronic acid) and an inorganic base to purified water and dissolving the mixture at an elevated temperature;

cooling the solution for crystallization; and filtering and vacuum drying the crystallized product.

In the addition step, the inorganic base is NaOH, $NaHCO_3$, $Na_2CO_3$, or the like and used in an amount of 1 equivalent. It is preferable that a dissolution temperature is 50 to 80° C., a cooling temperature in the cooling step is 5 to 30° C., and a cooling time is 2 to 5 hours.

In another aspect of the present invention, the process for preparing risedronate sodium hemipentahydrate is carried out by dissolving risedronate sodium anhydride with purified water at an appropriately elevated temperature, and cooling the solution. It is preferable that a dissolution temperature is 50 to 80° C., a cooling temperature is 5 to 25° C., and a cooling time is 2 to 5 hours.

In yet another aspect of the present invention, the process for preparing risedronate sodium hemipentahydrate is carried out by exposing risedronate sodium anhydride at a relative humidity of 60 to 90%. It is preferable that an atmospheric temperature is 30 to 40° C. and an exposing time is 4 to 20 hours.

The risedronate sodium hemipentahydrate obtained according to the present invention is in a crystalline form and contains water in a range of 11.9 to 13.9%.

Figure 1:
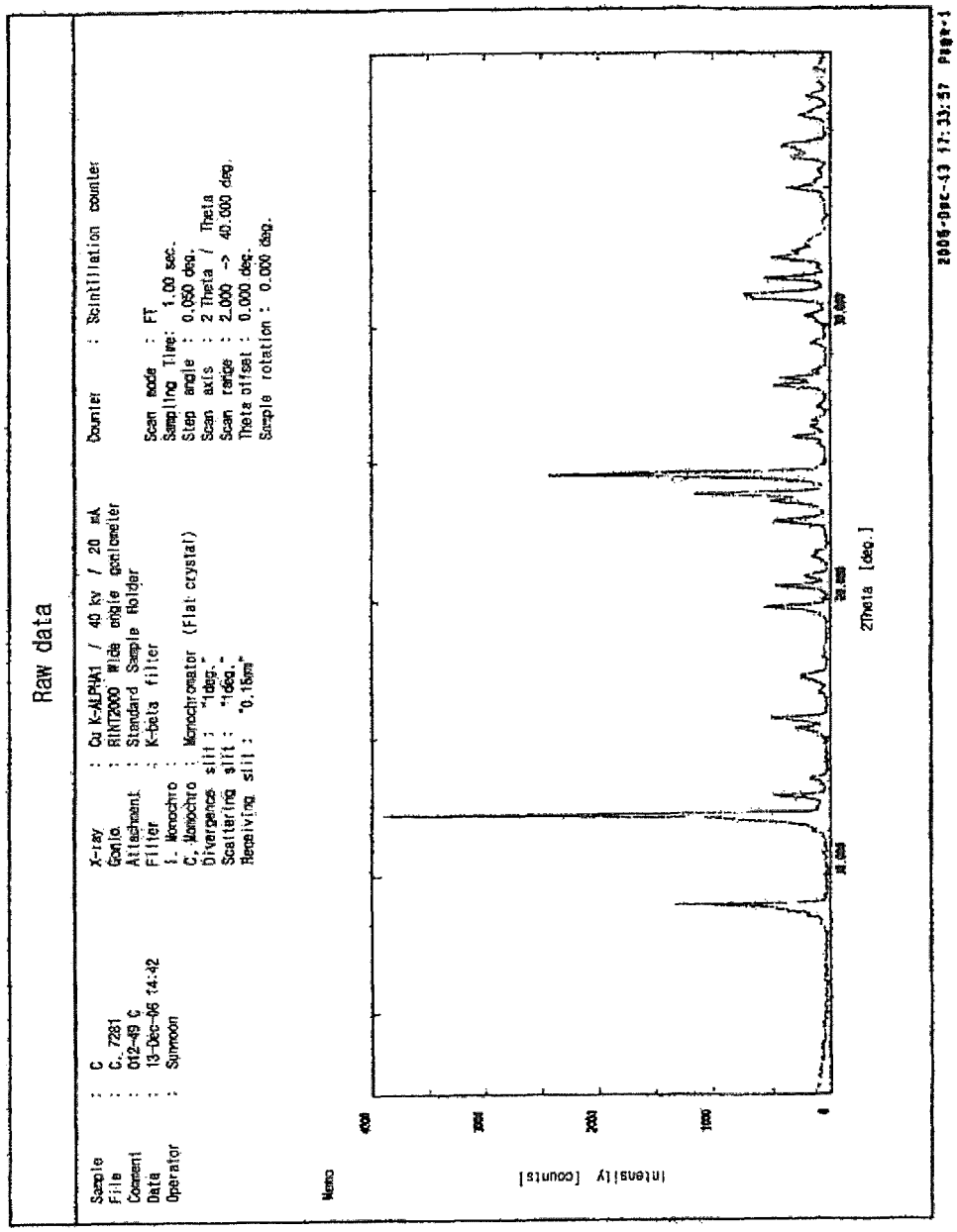
FIG. 1 illustrates X-ray powder diffraction pattern of risedronate sodium hemipentahydrate prepared according to the present invention.

FIG. 1 illustrates X-ray powder diffraction pattern of risedronate sodium hemipentahydrate prepared in the following Examples 1 to 3, in which x-ray peaks are recorded at 8.95, 12.20, and 24.55° 2θ.

Figure 2:
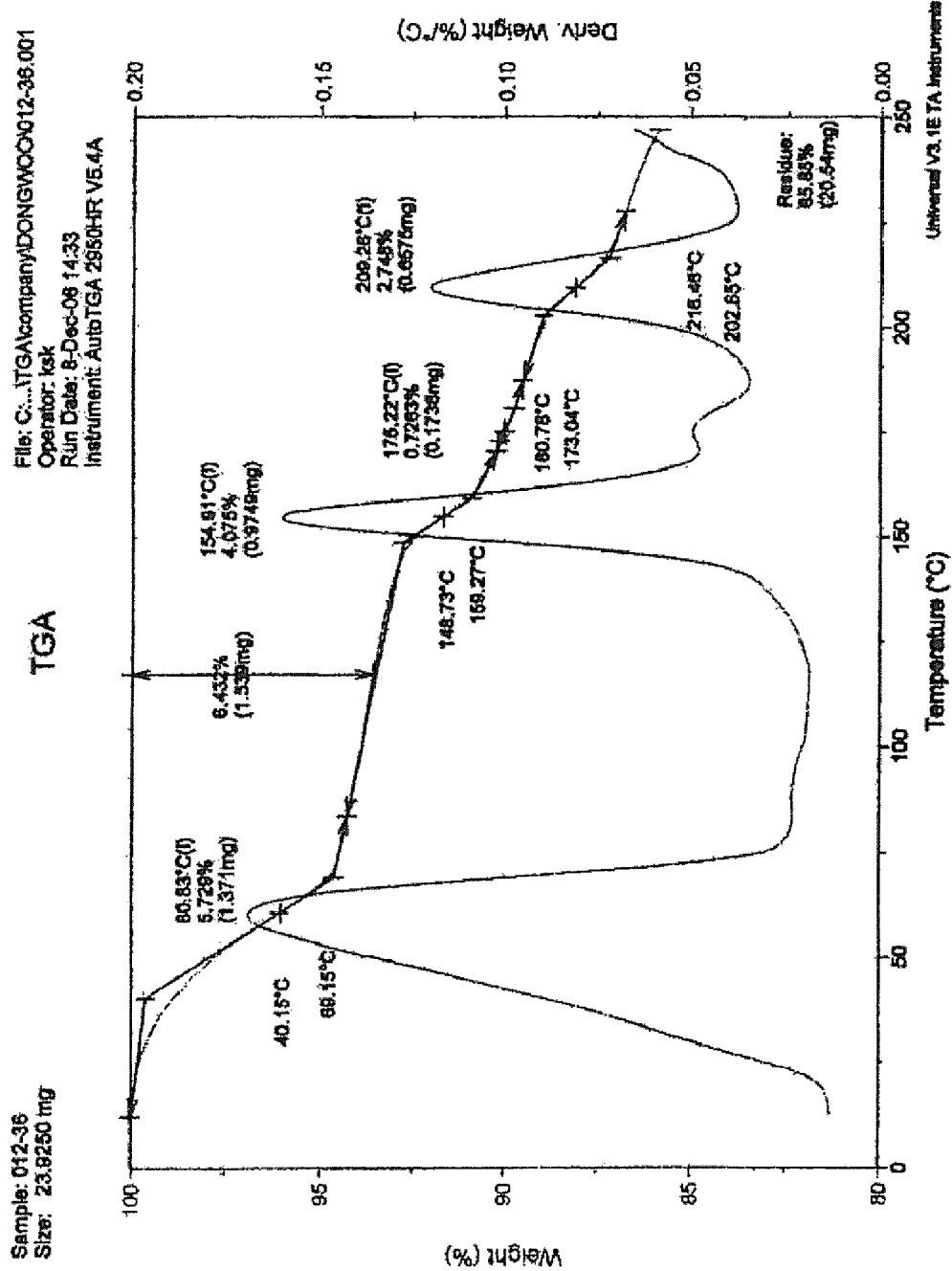
FIG. 2 illustrates TGA curve of risedronate sodium hemipentahydrate prepared according to the present invention.

FIG. 2 illustrates TGA curve of risedronate sodium hemipentahydrate prepared in the following Examples 1 to 3, in which the curve shows multiple weight loss steps for an overall weight loss of 12 to 14%.

The X-ray powder diffraction data is obtained by the powder diffraction method. The X-ray powder diffraction data is obtained by the well known method in this field of art using RIGAKU DMAX 2200 equipped with a solid state detector. The x-ray powder diffraction pattern of risedronate sodium hemipentahydrate is characterized by x-ray peaks at 8.95, 12.20, and 24.55° 2θ, and the other peaks at 12.90, 13.50, 15.70, 19.75, 22.85, 27.80, 28.10, 31.00, and 36.50° 2θ.

TGA weight loss is determined by calculating the weight loss over the temperature range up to about 200 to 220° C. at the inflection point of the weight loss curve. Thermogravimetric analysis (TGA) is a technique of thermal analysis well known in the art and measures the change in weight of a sample as a function of temperature. The technique is particularly well suited for measurement of, for example, decomposition and desolvation. TGA results of FIG. 2 were obtained using a TA Instrument and TGA 2950HR. Sample size was about 20 to about 40 mg. Samples were analyzed at a heating rate of 10° C./min from 25° C. to 250° C., The oven was purged with nitrogen gas at a flow rate of 40 ml/min. The TGA curve shows multiple weight loss steps, for an overall weight loss of 12 to 14%, which conforms to the value of 11.9 to 13.9% water content reported in Korean Patent Application No. 10-2002-7009790.

Hereinafter, the present invention will be described in more detail with reference to the following Examples. These examples are provided only for illustrating the present invention and should not be construed as limiting the scope and spirit of the present invention.

EXAMPLE 1

Preparation of Risedronate Sodium Hemipentahydrate

To 60 ml of purified water, 10.0 g of 2-(3-pyridyl)-1-hydroxyethane-1,1-bisphosphonic acid (risedronic acid) and 1.41 g of sodium hydroxide were added and dissolved at an elevated temperature of 65° C. After the dissolution, the resulting solution was cooled to 25° C. over 3 hours for crystallization. The obtained crystals were filtered and vacuum dried to obtain 8.0 g of risedronate sodium hemipentahydrate (64.7% of theoretical yield). (LOD by TGA=13.2%)

EXAMPLE 2

Preparation of Risedronate Sodium Hemipentahydrate

To 120 ml of purified water, 20.0 g of risedronate sodium anhydride was added and dissolved at an elevated temperature of 80° C. After the dissolution, the resulting solution was cooled to 25° C. for crystallization. The obtained crystals were filtered and vacuum dried to obtain 15.5 g of risedronate sodium hemipentahydrate (67.5% of theoretical yield). (LOD by TGA=13.3%)

EXAMPLE 3

Preparation of Risedronate Sodium Hemipentahydrate 10.0 g of risedronate sodium anhydride was exposed for 6 hours at a controlled RH of 85% and an atmospheric temperature of 35° C. to obtain 11.5 g of risedronate sodium hemipentahydrate (100% of theoretical yield). (LOD by TGA=13.4%)

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Industrial Applicability

The present invention relates to a novel process for preparing risedronate sodium hemipentahydrate using 2-(3-pyridyl)-1-hydroxyethane-1,1-bisphosphonic acid (risedronic acid) and an aqueous solution of risedronate sodium. The risedronate sodium hemipentahydrate is prepared using an eco-friendly preparation process with improved yield, low preparation cost, and barely any process waste. Thus, there is an advantage in industrial mass-production, and particularly, a product with very pure quality can be obtained in which the residual solvent in the product is remarkably improved since the preparation is carried out without using an organic solvent.

The invention claimed is:

1. A process for preparing risedronate sodium hemipentahydrate represented by formula 1,

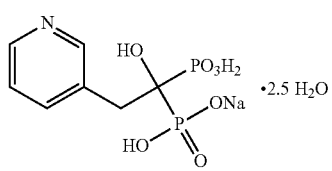

[Formula 1]

which consists of the steps of:
adding 2-(3-pyridyl)-1-hydroxyethane-1,1-bisphosphonic acid (risedronic acid) represented by formula 3:

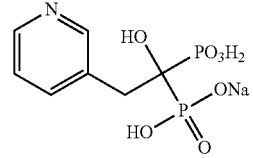

[Formula 3]

and an inorganic base to purified water and dissolving the mixture at a temperature of 50 to 80° C., provided that no solvent other than the purified water is added to the mixture;
cooling the solution to a temperature of 5 to 30° C. for crystallization; and
filtering and vacuum drying to obtain a crystallized product,
wherein the risedronate sodium hemipentahydrate product is crystalline having X-ray powder diffraction pattern as presented in FIG. 1, thermogravimetry analysis (TGA) as presented in FIG. 2, and contains water in a range from 11.9% to 13.9% by weight.

2. The process according to claim 1, wherein the inorganic base is NaOH, $NaHCO_3$, or $Na_2CO_3$.

3. The process according to claim 1, wherein the temperature is 60 to 70° C.

4. A process for preparing risedronate sodium hemipentahydrate which consists of the steps of:
dissolving risedronate sodium anhydride represented by formula 2:

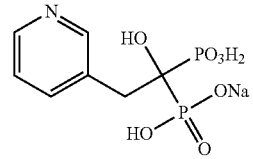

[Formula 2]

in purified water at a temperature of 60 to 80° C., provided that no solvent other than the purified water is added to the mixture; and
cooling the solution to a temperature of 5 to 25° C., wherein the risedronate sodium hemipentahydrate product is crystalline having X-ray powder diffraction pattern as presented in FIG. 1, thermogravimetry analysis (TGA) as presented in FIG. 2, and contains water in a range from 11.9% to 13.9% by weight.

5. A process for preparing risedronate sodium hemipentahydrate which comprises the step of exposing risedronate sodium anhydride at an atmospheric temperature of 30 to 40° C. and a relative humidity of 60 to 90% for 4 to 20 hours, wherein the risedronate sodium hemipentahydrate product is crystalline having X-ray powder diffraction pattern as presented in FIG. 1, thermogravimetry analysis (TGA) as presented in FIG. 2, and contains water in a range from 11.9% to 13.9% by weight.

* * * * *